United States Patent
Alivizatos

[11] Patent Number: 5,618,263
[45] Date of Patent: Apr. 8, 1997

[54] SOFT SPLINT

[75] Inventor: Margaret A. Alivizatos, Dallas, Tex.

[73] Assignee: Maurice Adam, Dallas, Tex.

[21] Appl. No.: 931,831

[22] Filed: Aug. 18, 1992

[51] Int. Cl.⁶ .................................... A61F 5/00
[52] U.S. Cl. ................ 602/6; 602/20; 602/23; 128/878; 128/882
[58] Field of Search ............... 602/6, 5, 13, 20–27, 602/8, 2, 1, 18, 61, 62, 63; 5/632, 636, 647, 652, 653; 128/401, 402, 878, 879, 881, 882

[56] References Cited

U.S. PATENT DOCUMENTS

| | | | |
|---|---|---|---|
| 3,212,497 | 10/1965 | Dickinson | 602/6 |
| 3,459,179 | 3/1966 | Oleson | 128/60 |
| 3,678,926 | 7/1972 | Strittmatter | 5/647 |
| 3,762,404 | 10/1973 | Sakita | 602/6 |
| 3,882,873 | 5/1975 | Arango | 128/402 |
| 4,213,213 | 7/1980 | Burnett | 5/653 |
| 4,393,520 | 7/1983 | Koch | 5/647 |
| 4,424,809 | 1/1984 | Yovankin | 602/62 |
| 4,527,556 | 7/1985 | Nelson | 602/27 |
| 4,657,003 | 4/1987 | Wirtz | 602/13 |
| 4,676,247 | 6/1987 | Van Cleve | 128/402 |
| 5,009,318 | 4/1991 | Lepinoy | 128/78 |
| 5,211,623 | 5/1993 | Sarkozi | 128/DIG. 23 |

Primary Examiner—Robert A. Hafer
Assistant Examiner—Brian E. Hanlon
Attorney, Agent, or Firm—Harris, Tucker & Hardin, P.C.

[57] ABSTRACT

A soft splint structure is wrappable around a patient's jointed limb. A plurality of interconnected elongated soft fabric sleeves are flexibly connected at their side edges to form a unitary structure. The sleeves define individual pockets which are partially filled with flowable lightweight expanded foam beads or other material which does not absorb moisture and freely passes air and moisture through the structure. The lightweight structure forms a soft splint which is wrappable around a patient's jointed limb and secured in place with a quick fastening means. The splint is quickly and easily installed and removed. When compressed, the sleeve members resist bending to keep a patient's limb in an unflexed extended position. In an extremely lightweight construction, the structure readily passes air and moisture therethrough and quickly dries in air after washing. Three or more sleeve members may be connected to form a splint having a suitably sized comfortable hollow semi-rigid splint which limits flexing of a joint.

22 Claims, 1 Drawing Sheet

SOFT SPLINT

BACKGROUND OF THE INVENTION

1. Field of the Invention

The invention is in the field of splints which limit bending of patient's joints to promote healing or prevent injury.

2. Background of the Prior Art

There are many circumstances where flexion of one or more of the patient's joints must be prevented or controlled. Often patients have suffered muscle or tissue damage in joints which normally flex or bend, such as elbows, knees, wrists and ankles. Such damage can be the result of twisting, especially on knees and elbows. Tendons may be torn or inflamed with tendinitis which makes bending of the injured joint excruciatingly painful.

The conventional art uses plaster or custom molded plastic splints to secure patients' joints from bending. Plaster of pads may be molded around the joint in a desired position and held until it dries and hardens into a hollow shape. Moldable plastic or combinations of plastic and plaster may be heated in hot water, bent into the desired shape, and held in place with gauze and adhesive tape. These conventional devices are hard and uncomfortable, especially because they do not permit adequate movement of air for drying and often create pressure points which cause decubitus pressure sores in extended use. Additionally, they are not reusable. The plaster must be cut off the patient and the plastic ones are custom molded to fit the particular patient's joint. The conventional devices block air flow and retain sweat around the joint. They are heavy, which adds to the discomfort, as anyone who has had to wear a plaster of pads splint can testify.

There is another category of patients for which no really effective splint is available. This is the category of patients suffering from neurological disorders or bad head injuries which suffer involuntary muscle contraction which causes prolonged flexion, especially of knees and elbows. Severe contracture of the elbow for a prolonged period during sleep can so pressure the ulnar nerve, by pinching at the elbow, that the entire hand and fingers can go numb. Also, some of these patients are disoriented and cannot be discouraged from pulling tubes that are necessary for their survival. Devices such as straight jackets are undesirable and uncomfortable as restraints, and normal splint devices are not easily installed and removed, as for example, between night and day operations.

It would be desirable to have a lightweight airy universal soft splint which can readily be wrapped around the patient's joint and secured to hold the limb in an extended position. Such a device should be quickly and easily removable and reusable by washing or sterilization and manufactured from readily available, inexpensive materials which are soft and comfortable against the skin, permit air movement around the joint and which does not require hardening into a massive structure.

SUMMARY OF THE INVENTION

A plurality of elongated soft fabric sleeves have spaced apart side edges and spaced apart ends which define a pocket or chamber in each sleeve which is adapted to receive sufficient filler material to form sleeves in the shape of flattened tubes, rounded between the side edges and closed at the ends. Lightweight filler material in each sleeve pocket forms the sleeves into structural sleeve members which resist bending of the sleeve members about their longitudinal axis. There is at least an inner and an opposite pair of outer sleeve members which are joined along the side edges to form an interconnected wrappable structure which may be wrapped around a patient's jointed limb to form a comfortable, hollow, semi-rigid soft splint which limits flexing of a jointed limb. A means for removably attaching the outer side edges of the pair of opposite outer sleeve members secures the wrappable structure around the patient's limb.

In one embodiment, the number of sleeve members is three, and in another embodiment, the number of sleeve members is four or more. A sufficient number of bendably connected sleeve members is used, sized to comfortably wrap around a patient's limb.

In another embodiment, an end of the sleeves has an openable closure to permit adding or removing filler material to increase or decrease fullness in order to tailor the shape of the sleeve member to the patient's needs. This helps make a custom fit in view of the fact that patients have limbs of different size which have to be wrapped. A greater resistance to bending is obtained with a fuller sleeve member.

The preferred filler material is a lightweight filler material comprising a multiplicity of discrete lightweight non-absorbent plastic foam beads sized to allow air and water to pass through the structure so that it will drain and dry quickly. An open mesh fabric, especially a synthetic open mesh fabric, such as a vinyl coated synthetic mesh fabric, aids in the ability of the entire structure to quickly drain and dry. Non-absorbent polystyrene foam beads are preferred.

The combination of a soft fabric and lightweight non-absorbent plastic foam beads, especially in combination with the open mesh fabric, allows air to freely circulate through the structure so that it remains cool and comfortable and moisture can evaporate from the skin. It has a unique characteristic that when the soft fabric sleeves are substantially filled with beads to a degree that allows free movement of the beads within the uncompressed sleeve members, they can be molded to fit the contour of the patient's limb, yet they have the characteristic that when the sleeve members and beads are compressed by wrapping the wrappable structure around the patient's jointed limb and securing a means for removably attaching, they interact to lock together in the previously molded shape to significantly resist bending while allowing circulation of air and moisture to help keep the patient's joint securely positioned and dry.

The soft splint may be made from separate sleeves bendably joined together along the side edges to form the splint structure, or fabricated from a pair of generally rectangular fabric panels which are placed in juxtaposition, joined around the marginal edges to form one large pocket for filler material and provided with hinge-like transverse seams connecting the first and second textile panels at a plurality of spaced apart locations dividing the large pocket into a plurality of smaller pockets for receiving filler material. When the filler material is added to smaller pockets, an equal plurality of hingedly connected structural panels are created which form the wrappable structure. This structure may also be created by folding over onto itself a textile panel having twice the normal length before the marginal and transverse seams are made. A zipper along one edge across the ends of the sleeves provides a convenient openable closure for adding or removing filler material, as desired.

In another embodiment, one of the panel members can have an outside surface comprising the hook and loop material commonly sold under the trademark VELCRO® whereby corresponding VELCRO® straps along an opposite transverse outside edge may be used to secure the structure in the wrapped position instantaneously by contact with the VELCRO® surface. As a variation of this, the opposite transverse outside edge may have a single VELCRO® strap having its long side edge attached to the transverse side edge of an outside panel, running along the edge, to secure the entire side edge in the wrapped position by contact with a corresponding VELCRO® surface or a patch of VELCRO® arranged to receive and hold the strap when the structure is wrapped around a limb.

DETAILED DESCRIPTION OF THE PREFERRED EMBODIMENT

Figure 1:
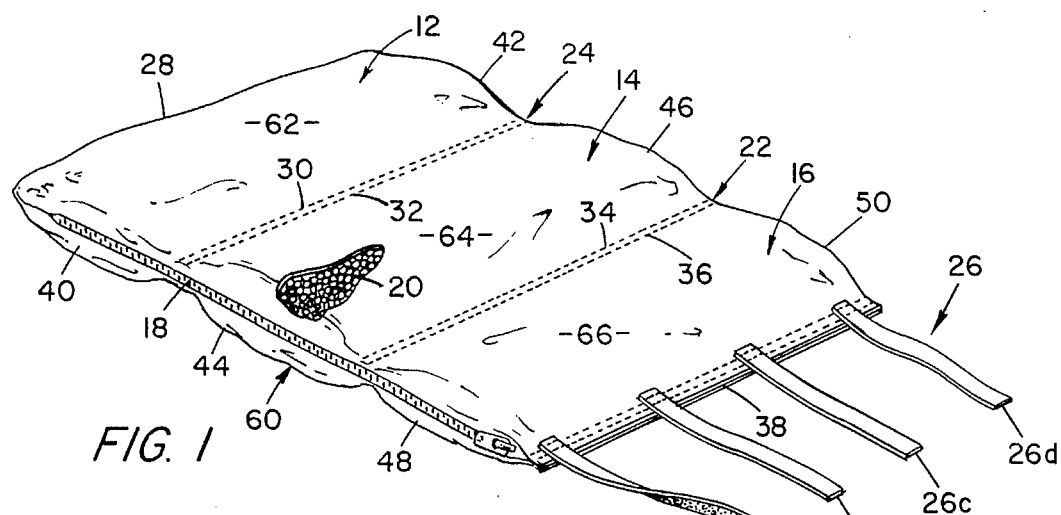
FIG. 1 is a perspective view of a tripartite soft splint having an inner sleeve member between a pair of opposite outer sleeve members, partially cut away to show the plastic bead filler material inside.

A tripartite embodiment of the soft splint is generally designated by the reference numeral 10 in FIG. 1. Soft splint 10 comprises elongated soft fabric sleeves 12,14,16 having spaced apart side edges and spaced apart ends which define a pocket in each sleeve adapted to receive sufficient filler material to form sleeve members in the shape of flattened tubes rounded between the side edges and closed at the ends. An outer sleeve 12, an inner sleeve 14, and an outer sleeve 16 will be referred to as sleeve members 12, 14 and 16 when they contain filler material. In the flattened, unfilled condition, they may be referred to as sleeves 12, 14 and 16.

Soft splint 10 has an openable closure 18 which extends along one end of the sleeve members. Inner sleeve member 14 is cut away to show a preferred filler material comprising plastic foam beads 20. Inner sleeve member 14 is connected to outer sleeve member 16 by means for flexible bendable connection 22 and to outer sleeve member 12 by means for flexible bendable connection 24. Means for bendable connection 22,24 may be formed by seaming longitudinal side edges of one sleeve member to a longitudinal side edge of each adjacent sleeve member.

Fabric sleeve 12 is defined by outer side edge 28, longitudinal side edge 30 and opposite ends 40 and 42. Fabric sleeve 14 is defined by longitudinal side edge 32, longitudinal side edge 34 and opposite end portions 44 and 46. Fabric sleeve 16 is defined by longitudinal side edge 36, outer side edge 38 and opposite end portions 48 and 50. A means for removably attaching 26 is connected to one of the outer side edges 28,38 comprising a plurality of strap members 26a–d attached at intervals along outer side edge 38. The pocket in sleeve 12 may be formed within juxtaposed upper and lower rectangular shaped panels 62 which are defined by the outer boundaries 28,30,40 and 42 which define the sleeve. Similarly, the pocket in sleeve 14 may be defined by juxtaposed upper and lower fabric panels 64 and the pocket in sleeve 16 may be defined by juxtaposed upper and lower panels 66.

Figure 4:
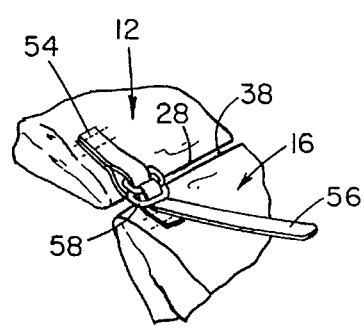
FIG. 4 is a perspective view showing a buckle on the outside surface of the outer transverse edges of a soft splint which may be used to removably secure the outer edges together.

Removable attaching means 26 is preferably made from conventional hook and loop material 27 commonly available and sold under the trademark VELCRO®, which removably engages a corresponding hook and loop material on one of the panels 62 of the opposite outer sleeve member 12. Alternately, in FIG. 4 is shown a cutaway portion of connected outer sleeve members 12,16 which includes a means for attaching comprising a plurality of strap loops 54 on member 12 and corresponding straps 56 on member 16 which are interconnected through conventional "D" rings 58. Various types of fastening means may be employed, but it is important that they be easily attached and detached removably to secure the wrappable structure around a patient's jointed limb to form a comfortable hollow semi-rigid soft splint which limits flexing of the jointed limb as in FIG. 2. To reduce the chance of deliberate removal by an uncooperative patient, the whole splint may be secured all around by wrapping with adhesive tape.

Figure 2:
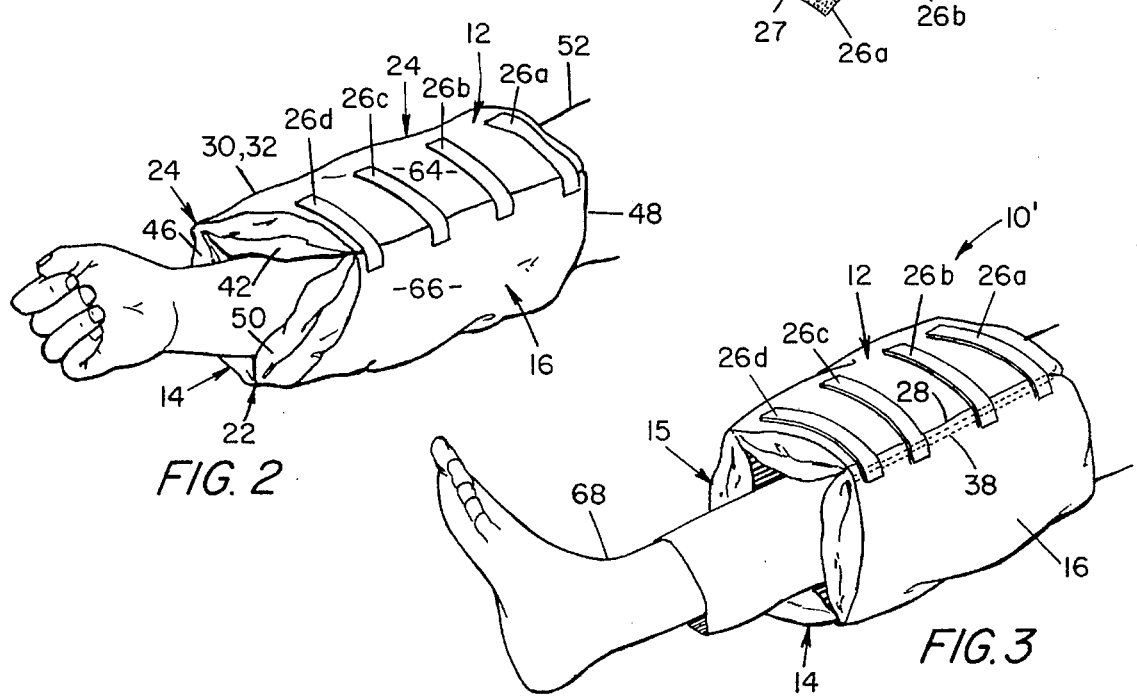
FIG. 2 shows the wrappable structure of FIG. 1 wrapped and secured around the patient's elbow to hold it in the extended position.

FIG. 2 shows the wrappable structure of FIG. 1 which has been turned over and wrapped around the elbow of a patient's arm 52. Here it is seen that the bendable connections 22,24 are bent so that soft splint 10 is wrapped around the patient's elbow and fastening means 26a–d are attached after soft splint 10 is wrapped around the elbow. Outside edges 28,38 are thereby drawn up into contact with each other and zipper 18 is now hidden on the opposite end of splint 10.

A particular advantage of the openable closure is that it permits adding or removing filler material 20 to increase or decrease fullness in order to tailor the shape of the sleeve members 12,14,16, to the patient's needs. One aspect of the variability in fullness is to accommodate the known variation in outside diameter of the arms of different patients. This makes it possible for one size to fit a variety of different patients. Another aspect of the ability to increase or decrease fullness is the effect it has upon the ability to withstand bending. It may be seen that sleeve members 12,14,16 having filler within the pockets comprise hingedly connected structural panels which resist bending. They may be visualized as each having a longitudinal axis parallel to the longitudinal side edges 28–38 in the geometrical center. The bending resistance is proportional to the thickness of the panels and that thickness is provided by the filler material.

If only a relatively small amount of filler material is placed in the pocket, the sleeve members will be relatively thin and flat and consequently will offer less bending resistance than if additional filler material is added to make them "fatter" and thicker in height. This makes it possible to adjust the amount of flexing that an individual patient can comfortably exercise while still maintaining the limb in an essentially extended position and preventing contracture. The amount of bending of the longitudinal axis is reduced when more filler material is added. The effect is enhanced by interaction that occurs between the textile cover of the pockets and the foamed plastic beads used as filler material.

The sleeve member pockets are preferably filled somewhat loosely with the free flowing plastic beads so that the panels can be molded around the patient's swollen joint to conform to the body contour. When the sleeve member and beads are compressed by wrapping the wrappable structure around a patient's joint or limb and attached by the straps, the fabric and beads interact with each other to lock together in the previously molded shape to significantly resist bending yet allow circulation of air and moisture to help keep the patient dry. This is an important comfort factor. This makes it possible to comfortably conform to variations in shape of the patient's elbow or knee even if it contains protrusions or swellings because of tissue, tendon or cartilage damage. The splint conforms to an irregular shape. The interaction between the fabric cover and the beads causes the beads to act as though they were a solid material, presumably because of increased friction which occurs because of compression. Once compression is released by undoing the straps, the soft splint is easily bendable unless it is filled to an extent that itself creates compression between the fabric and the beads. Not only does the soft splint accommodate the patient's irregular shaped limb, but once it is attached, it comfortably becomes rigid under compression.

Even if it is not filled or compressed to an extent where a complete wrap around the limb permits the splint to become rigid, it becomes rigid as soon as the patient begins to bend the limb because that action tends to reduce the volume and induces compression between the fabric cover and the beads. This is an important characteristic which no conventional splint provides. While it is true that a plaster cast will conform to the patient's elbow or knee structure, there is no effective way to provide the medical practitioner or the patient himself with the ability to adjust the degree of permissible motion by the simple operation of adding or removing beads. The feather-light construction is a joy to wear compared to the heavy plaster cast or molded hard plastic splints which are commonly used. A further advantage is that there is no danger of damaging either patient or objects around the patient from accidental bumping because the soft splint 10 is indeed soft, as compared to plaster, and serves as a cushion to absorb shock and prevent further injury.

The soft splint may be constructed from soft, flexible natural or synthetic fabric in a number of ways. One method of construction is to form individual upper and lower elongated panels 62,64,66 into sleeves by seaming around their marginal edges and then hingedly joining their longitudinal side edges to create a unitary soft splint 10. In this case, it might be convenient to have individual openable closures in one end of each of the members 12,14 and 16. Another way is to have a common soft fabric base panel 60 having opposite side edges correspond to the outer side edges 28,38 of the opposite outer sleeve members. Upper panels 62,64,66 can be placed over base panel 60 with seams forming the edges of the pockets and the means for bendable connection being formed by seams extending across the fabric base panel spaced apart and parallel to the outer side edges.

Another method of making the soft splint 10 is to have a first textile covering and a matching second textile covering of generally rectangular shape placed together having inside surfaces facing each other and joined around the marginal edges to form one large pocket for filler material. Then hinged transverse seams connecting the first and second textile covers are placed at a plurality of spaced apart locations dividing the large pocket area into a plurality of smaller pockets for filler material. These would correspond to the seams 22,24 in FIG. 1. Then with filler material placed within the plurality of smaller pockets is created an equal plurality of hingedly connected structural panels 12,14,16 including opposite end panels 12,16 and at least one middle panel 14. This can be accomplished from a single sheet of soft fabric which is folded over onto itself so that one of the outer edges 28,38 comprises a marginal folded edge rather than a seamed marginal edge.

The upper and lower panels may be of different materials selected for comfort and economy. One variation of this would be to have at least upper panel 62 made of the hook and loop material so that when the splint is wrapped around, the straps 26 will "stick" to the surface of sleeve member 12. Alternately still, the straps 26a–d may be formed as a single strap extending all along edge 38 from the location of strap 26a to the location of strap 26d extending outwardly away from edge 38 only about ⅓ to ½ of the length of straps 26 shown in FIG. 1. This would add a significant additional resistance to bending or coming loose by increasing the holding area of the fastening means. It also avoids the necessity of dealing with individual straps 26a–d and makes the device still easier to install and remove.

Figure 3:
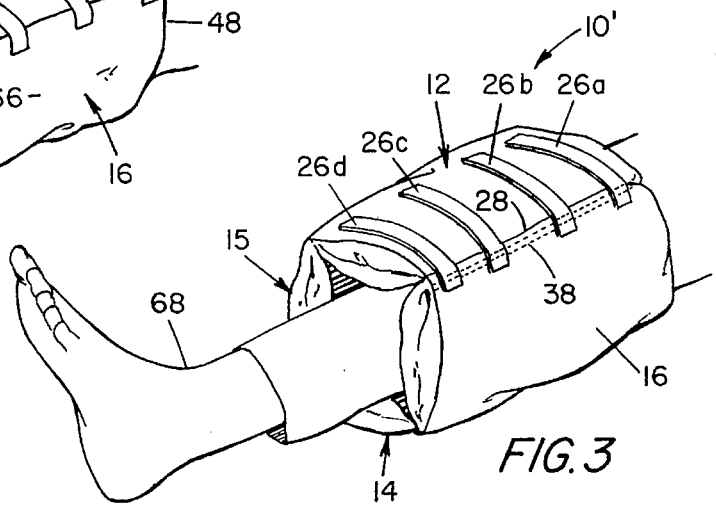
FIG. 3 shows a soft splint having four sleeve members wrapped and secured around a patient's knee to hold it in the extended position.

While the soft splint has been heretofore described as comprising three sleeve members, the invention is not limited to three sleeve members as is indicated in FIG. 3. FIG. 3 shows that one or more additional inner sleeve members may be added to create more of a square or box-like shape or to provide a larger enclosure for a knee of a patient's leg 68. An additional sleeve member 15 is interposed between sleeve members 12 and 14 to provide four sleeve members in modified sleeve member $10^1$. Additional sleeve members could be added which would tend to create a pentagonal or hexagonal interior shape. Alternately, a zipper could be provided all along outer edge 28 of panel 12 of FIG. 1 and a corresponding zipper on an individual panel 15, one part on each so that a three part soft splint 10 could be converted into a four part soft splint $10^1$ simply by fastening the zippers to connect panels 12 and 15 along edge 28. By additional zippered sleeves, more than one additional panel could be added if desired.

An important characteristic of the structure is that water passes through the entire structure and it dries rapidly. The skin stays dry, decreasing the risk of decubitii. The soft splint is completely washable, does not need drying and does not lose its shape with repeated laundering. Any shrinkage of the plastic beads 20 caused by repeated machine drying is easily accommodated by the simple expedient of opening the structure and adding additional beads. In the best mode, the plastic beads are preferably spherical resilient plastic beads formed from expanded cellular plastic expanded to a diameter in the range of about 0.062" to 0.018" which are substantially liquid impermeable and extremely lightweight. The preferable material for the beads is polystyrene which have a closed cell construction. They will not retain moisture or harbor bacteria and are mold and mildew resistant. The fabric should also be mold and mildew resistant.

The soft fabric is preferably a cotton fabric on the side in contact with the skin, having an open mesh construction to facilitate the passage of air and water. An open mesh synthetic fabric may be used on either or both sides of the structure to still further facilitate washing and quick drying characteristics. Suitable synthetic fabric has been provided by Intex Plastics Corp., P.O. Box 957, Golding Drive, Corinth, Miss. 33834. An open mesh fabric having an 18×15 thread per inch polyester scrim base with a respective denure of 600×840 coated with PVC vinyl has been used successfully. Such fabric has a total thickness of about 0.016" and weighs about 9 ounces per square yard. A vinyl coated fabric or fabric coated with a skin compatible friction increasing coating has an additional advantage in that it increases the coefficient of friction which tends to increase any resistance to slipping when the structure is wrapped around a patient's limb and secured. The typical length of the splint running along the patient's limb would be in a range of 12–14" with individual sleeve members being about 3–4" wide. The size can be scaled down appropriately for the smaller sized limbs of children and even for pediatric use. Although foam plastic beads are the preferred filler material, the pockets can be filled with appropriately shaped solid "boards" of preferably lightweight non-absorbent plastic or other materials, such as padded slats, which have sufficient bending resistance. Even when the pockets of the sleeves have the plastic foam beads, extra rigidity can be provided by inserting slats of plastic or wood in such a way that comfort is not defeated, by maintaining a layer of the softer beads against the patient, under the slats.

I claim:

1. A soft splint structure for limiting flexion of a patient's jointed limbs, comprising:

a plurality of interconnected elongated soft fabric sleeves forming a wrappable soft splint structure, the sleeves having juxtaposed panels having spaced apart side edges and spaced apart ends which define a pocket in each sleeve adapted to receive sufficient filler material to form sleeve members in the shape of flattened tubes rounded between the side edges and closed at the sides and ends which allow the circulation of air and moisture;

the sleeve pockets being loosely filled with sufficient lightweight plastic foam bead filler material comprising a multiplicity of discrete lightweight non-absorbent plastic foam beads contained within each sleeve, substantially filling said sleeves to a degree that allows free movement of the beads within the uncompressed sleeve members, to form the sleeves into sleeve members formed as flattened tubes rounded between the side edges and closed at the sides and ends, so that the sleeve members can be molded to fit the contour of the patient's limbs;

said sleeve members resisting bending in response to being wrapped and secured around a patient's limb, said sleeve members and a sufficient amount of said plastic foam bead filler material contained therein to have the characteristic that when the sleeve members and beads are compressed when the wrappable structure is wrapped around and compressed against a patient's jointed limb and held by a means for removably attaching, they interact to lock together in a previously molded shape to significantly resist bending and allow circulation of air and moisture therethrough to help keep the patient dry;

the wrappable soft splint structure having bendable connections of the sleeve members to each other along the interconnected side edges of the sleeve members and having at least one inner and a pair of opposite outer sleeve members, and means for removably attaching the outer side edges of the opposite outer said sleeve members around a patient's limb to removably secure and compress the wrappable structure around a patient's limb to form a comfortable hollow semi-rigid soft splint structure around a patient's limb which limits flexing of a jointed limb.

2. The soft splint of claim 1 further including an openable closure in the sleeve members to permit adding or removing filler material to increase or decrease fullness in order to tailor the shape of the sleeve members to the patient's needs.

3. The soft splint of claim 2 wherein said closure is a zipper located on an end of said sleeve members.

4. The soft splint of claim 1 wherein said bendable connections are formed by seaming longitudinal side edges of one sleeve member to a longitudinal side edge of each adjacent sleeve member.

5. The soft splint of claim 4 wherein said means for removably attaching comprises a plurality of straps mounted along the outer side edge of an outer sleeve member.

6. The soft splint of claim 5 wherein said plurality of straps comprise hook and loop material straps which engage hook and loop material on a surface of the opposite outer sleeve member to secure the wrappable splint.

7. The soft splint of claim 1 wherein said plurality of elongated soft fabric sleeves are formed along a common soft fabric base panel having opposite side edges that correspond to the outer side edges of the opposite outer sleeve members and said bendable connections are formed by seams extending across said fabric base panel, spaced apart and parallel to said outer side edges.

8. The soft splint of claim 7 wherein the fabric used to make the sleeves and base panel has an open mesh construction to readily allow the passage of air and fluid for quick drying.

9. The soft splint of claim 8 wherein said lightweight non-absorbent plastic foam beads are sized to allow air and water to pass through the structure in use and so that it will drain and dry quickly.

10. The soft splint of claim 9 wherein said plastic foam beads are non-absorbent polystyrene foam beads.

11. The soft splint of claim 10 wherein said beads have a variation in size of an order of magnitude for purposes of good close packing characteristics.

12. The soft splint of claim 11 wherein the fabric is a mold and mildew resistant open mesh synthetic fabric that is non-absorbent.

13. The soft splint of claim 8 wherein the fabric is a mold and mildew resistant open mesh synthetic fabric that is non-absorbent.

14. The soft splint of claim 8 wherein said fabric is an open mesh synthetic vinyl-coated fabric.

15. The soft splint of claim 1 wherein said beads are non-absorbent polystyrene foam beads.

16. The soft splint of claim 15 wherein the fabric is a mold and mildew resistant open mesh synthetic fabric that is non-absorbent.

17. The soft splint of claim 16 wherein said fabric is an open mesh synthetic vinyl-coated fabric.

18. A soft splint for limiting flexion of joints in a patient's limbs, comprising;

a first textile covering and a coextensive matching second textile covering of generally rectangular shape each having inside and outside surfaces placed together with the inside surfaces facing each other and joined around the marginal edges to form one large fabric pocket for filler material;

transverse seams connecting the first and second textile covering at a plurality of spaced apart locations and hingedly dividing the large fabric pocket into a plurality of smaller fabric pockets for filler material;

filler material placed within the plurality of smaller pockets to create an equal plurality of hingedly connected structural panels, including opposite end panels and at least one middle panel;

said lightweight filler material being a multiplicity of discrete lightweight non-absorbent plastic foam beads contained within said hingedly connected structural panels and substantially filling said structural panels to a degree that allows free movement of the beads within the uncompressed structural panels so that the uncompressed structural panels can be molded to fit the contour of the patient's limbs, yet having the characteristic that when the structural panels and beads are compressed by tightly wrapping said structural panels around a patient's jointed limb they interact to lock together in the previously molded shape to significantly resist bending and allow circulation of air and moisture therethrough to keep the patient dry: and means for quickly and easily fastening and unfastening the outer marginal transverse edges of the opposite hingedly connected structural end panels around a patient's jointed limb to form a wrappable hollow semi-rigid soft splint which is compressed around a patient's limb to become rigid and comfortably limit flexing of the limb.

19. The soft splint of claim 18 wherein said lightweight non-absorbent plastic foam beads are sized to allow air and water to pass through the structure in use and so that it will drain and dry quickly.

20. The soft splint of claim 19 wherein the fabric is a mold and mildew resistant open mesh synthetic fabric that is non-absorbent.

21. The soft splint of claim 18 further including an openable closure in the smaller pockets to permit adding or removing filler material to increase or decrease fullness in order to tailor the shape of the smaller pockets to the patient's needs.

22. The soft splint of claim 21 wherein the fabric is a coated open mesh fabric which has an increased friction which, when the structure is wrapped around a patient's limb, keeps the wrapped structure from slipping as compared with an uncoated fabric.

* * * * *